United States Patent
Mandimutsira et al.

(10) Patent No.: US 9,765,005 B2
(45) Date of Patent: Sep. 19, 2017

(54) METHODS OF USING HOMOGENOUS RHODIUM CATALYSTS WITH N-HETEROCYCLIC CARBENE LIGANDS FOR THE HYDROFORMYLATION OF OLEFINS AND SUBSTITUTED OLEFINS

(71) Applicant: Lyondell Chemical Technology, L. P., Houston, TX (US)

(72) Inventors: Beaven S. Mandimutsira, Houston, TX (US); Daniel F. White, Houston, TX (US); Brian A. Salisbury, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 14/481,528

(22) Filed: Sep. 9, 2014

(65) Prior Publication Data

US 2016/0068458 A1     Mar. 10, 2016

(51) Int. Cl.
*C07C 45/50* (2006.01)
*C07C 29/16* (2006.01)
*B01J 31/22* (2006.01)
*B01J 31/20* (2006.01)

(52) U.S. Cl.
CPC ............... *C07C 45/50* (2013.01); *B01J 31/20* (2013.01); *B01J 31/2213* (2013.01); *B01J 31/2295* (2013.01); *B01J 2231/321* (2013.01); *B01J 2531/822* (2013.01)

(58) Field of Classification Search
CPC ................................ C07C 45/50; C07C 29/16
USPC ........................................ 568/454, 460, 909
See application file for complete search history.

(56) References Cited

U.S. PATENT DOCUMENTS

| | | | | |
|---|---|---|---|---|
| 6,127,584 A | * | 10/2000 | Zajacek et al. | 568/852 |
| 7,279,606 B1 | * | 10/2007 | White | 568/454 |
| 7,442,842 B2 | * | 10/2008 | Jakel et al. | 568/451 |
| 2012/0132537 A1 | * | 5/2012 | Sivasankar et al. | 205/439 |

OTHER PUBLICATIONS

International Search Report and Written Opinion for PCT/US2015/048931 dated Nov. 26, 2015.
Jackson D. Scholten et al., Organometallics, vol. 27, pp. 4439-4442, 2008.
Jeremy M. Praetorius et al., Organometallics, vol. 26, pp. 1057-1061, 2007.
Charles U. Pittman et al., J. Org. Chem., vol. 45, pp. 2132-2139, 1980.
Adam S. Veige, Polyhedron, vol. 27, pp. 3177-3189, 2008.

* cited by examiner

*Primary Examiner* — Sikarl Witherspoon

(57) ABSTRACT

A method of using homogenous rhodium catalysts comprising N-heterocyclic carbene ligands for the hydroformylation of olefins and substituted olefins is provided. In some aspects, the methods provided herein relate to the hydroformylation of allyl alcohol to 4-hydroxybutaldehyde in the presence of a rhodium catalyst which contains one or more N-heterocyclic carbene ligands of the formula:

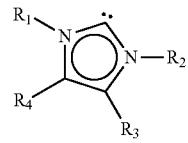

wherein $R_1$, $R_2$, $R_3$, and $R_4$ are defined herein.

15 Claims, No Drawings

METHODS OF USING HOMOGENOUS RHODIUM CATALYSTS WITH N-HETEROCYCLIC CARBENE LIGANDS FOR THE HYDROFORMYLATION OF OLEFINS AND SUBSTITUTED OLEFINS

BACKGROUND OF THE INVENTION

I. Field of the Invention

The present disclosure relates generally but not exclusively to novel methods of using homogenous rhodium catalysts comprising N-heterocyclic carbene ligands for the hydroformylation of olefins and substituted olefins, including for example, the use of (acac)(CO)Rh-Imes as a catalyst for the selective hydroformylation of allyl alcohol to 4-hydroxybutyraldehyde (HBA). Further aspects and specific embodiments of the disclosure are provided below.

II. Description of Related Art

Hydroformylation is a significant and commercially important process in which an alkene is reacted with carbon monoxide and hydrogen to form an aldehyde. (Leeuwen and Claver, 2000). This transformation is an industrially important process, which is used to produce compounds such as 4-hydroxybutyraldehyde (HBA), which is in turn used in the synthesis of 1,4-butanediol. See, for example, U.S. Pat. Nos. 4,065,145, 4,215,077, 4,238,419, 4,567,305, 4,678,857, 5,290,743, and 7,790,932. Rhodium-based complex with phosphine ligands are commonly-used catalysts for hydroformylations. Phosphine ligands have been shown to affect the selectivity as well as the reactivity of the metal catalyst depending on the structure of the ligand (Evans, et al., 1968a; Evans, et al., 1968b; U.S. Pat. No. 3,239,569; U.S. Pat. No. 3,239,570; Slaugh and Mullineaux, 1968; Yagupsky, et al., 1969; Brown and Wilkinson, 1969; Brown and Wilkinson, 1970).

While hydroformylation was discovered decades ago, many challenges remain, including minimizing the formation of undesired co-products and byproducts (Coloquhuon, et al., 1991), preventing catalyst degradation, addressing the sensitivity of the phosphine ligands that are typically used to oxidation (Pruett, et al., 1979), and identifying reaction conditions that do not require the presence of a large excess of phosphine ligand (Brown and Wilkinson, 1969; Brown and Wilkinson, 1970; Hjortkjaer, 1979). Reducing the byproducts and co-products also remains a challenge in the production of the HBA. One such co-product is 3-hydroxy-2-methylpropionaldehyde (HMPA), which is a branched isomer of HBA. While not all co-products are necessarily undesirable, the application of additional energy- and/or capital-intensive steps is typically required to separate them for the main product. The generation "$C_3$-byproducts" such as n-propanol and propionaldehyde also continues to remain a challenge. All side products, regardless of whether they are byproducts or co-products, are produced at the expense of the main product, thereby impacting the overall reaction yield.

In order to improve the production 1,4-butanediol, numerous studies have explored the desired properties of the ligand in order to raise the yield of the desired hydroformylation product. Many of the efforts have been directed towards identifying the optimal ligand type, concentration, and substitution pattern. For example, U.S. Pat. No. 6,127,584 reports the use of a trialkyl phosphine ligand containing at least two methyl groups as one method of improving the ratio of HBA to HMPA. Furthermore, diphosphine ligands such as DIOP, XANTPHOS, or trans-1,2-bis(diphenylphosphinomethyl)cyclobutane have been explored and shown to be effective in improving the HBA:HMPA ratio in studies discussed in Japan Kokai Nos. 06-279345 and 06-279344 as well as in the U.S. Pat. No. 4,306,087. Moreover, studies have been carried out using complex butane and cyclobutane ligands as disclosed in U.S. Pat. Nos. 7,271,295 and 7,279,606. Other studies have explored other components of the reaction such as the concentration and pressure of the carbon monoxide and its effect on the overall production of specific products. The concentration of CO, for example, was identified by U.S. Pat. No. 6,225,509 to play a significant role in the production of byproducts and co-products.

In spite of the advances that have been made, the development of new catalytic hydroformylation processes remains desirable. Depending on the production requirements and desired product specifications, different process parameters and characteristics will be of greater/lesser importance. Such parameters and characteristic include improved product selectivity, energy efficiency, catalytic activity, catalyst turn over number, and catalyst life. The reduction and/or elimination of waste products, atom economy, and improved product yield and purity also remain important considerations. By providing novel hydroformylation processes that offer different product and reaction profiles, additional flexibility is provided for addressing one or more of the challenges faced in the production of hydroformylation products, including HBA.

SUMMARY OF THE INVENTION

In one aspect of the present disclosure, there are provided novel methods of using a homogenous rhodium catalyst comprising a N-heterocyclic carbene ligand for the hydroformylation of olefins and substituted olefins, including, for example, the use of (acac)(CO)Rh-Imes as a catalyst for the selective hydroformylation of allyl alcohol to 4-hydroxybutyraldehyde (HBA).

In another aspect, the present disclosure provides a method for the hydroformylation of a terminal alkene$_{(C \leq 12)}$ or a substituted terminal alkene$_{(C \leq 12)}$ to make an aldehyde, comprising a step of reacting the terminal alkene$_{(C \leq 12)}$ or the substituted terminal alkene$_{(C \leq 12)}$ with carbon monoxide (CO) and hydrogen ($H_2$) in a reaction mixture comprising a rhodium complex and an N-heterocyclic carbene ligand to produce an aldehyde$_{(C \leq 13)}$ or a substituted aldehyde$_{(C \leq 13)}$. In some embodiments, the terminal alkene$_{(C \leq 12)}$ or substituted terminal alkene$_{(C \leq 12)}$ is allyl alcohol. In some embodiments, the aldehyde$_{(C \leq 13)}$ or substituted aldehyde$_{(C \leq 13)}$ is 4-hydroxybutyraldehyde. In some embodiments, the rhodium complex is a rhodium(I) complex with no halide ligands. In some embodiments, the rhodium complex is Rh(CO)$_2$(acac), Rh(CO)$_2$COD, Rh(CO)$_2$(PPh$_3$), or RhOAc. In some embodiments, the N-heterocyclic carbene is further defined by the formula:

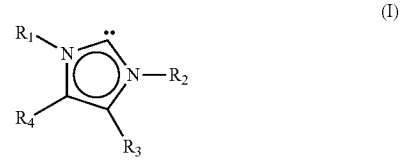

(I)

wherein: $R_1$ and $R_2$ are each independently alkyl$_{(C \leq 12)}$, aryl$_{(C \leq 42)}$, aralkyl$_{(C \leq 42)}$, or a substituted version of any of these groups; $R_3$ and $R_4$ are each independently hydrogen, halo, hydroxy, cyano, nitro, amino, or alkyl$_{(C \leq 12)}$, aryl$_{(C \leq 12)}$, aralkyl$_{(C≤12)}$, or a substituted version of any of these groups; or R$_3$ and R$_4$ are taken together and are alkanediyl$_{(C≤12)}$, alkenediyl$_{(C≤12)}$, or a substituted version of either of these groups. In some embodiments, the N-heterocyclic carbene is further defined as:

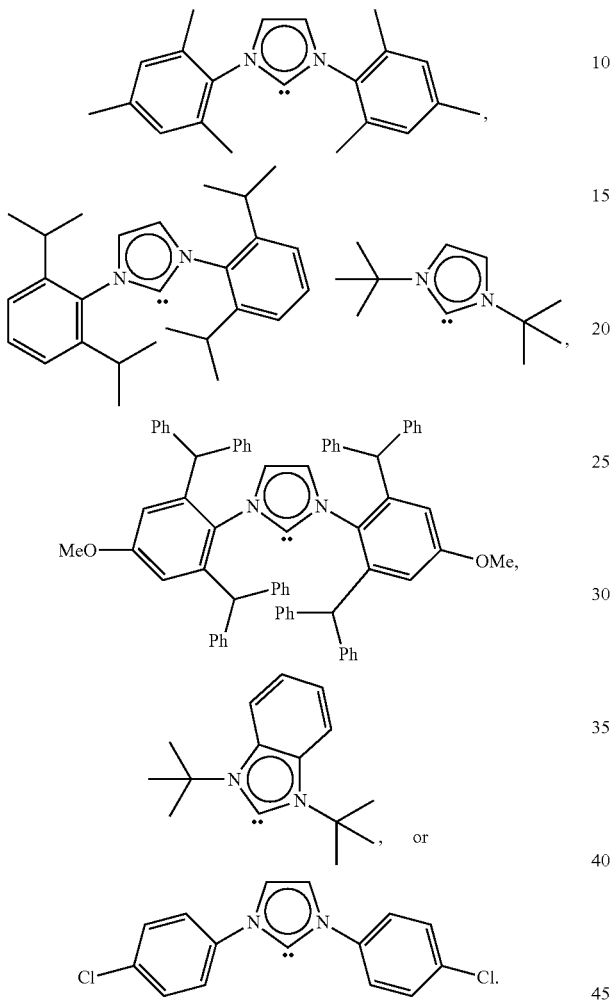

In some embodiments, the reaction mixture further comprises a first auxiliary ligand, wherein the first auxiliary ligand is a phosphine$_{(C≤30)}$, a diphosphine$_{(C≤50)}$, a phosphite$_{(C≤30)}$, a diphosphite$_{(C≤50)}$, or a substituted version of any of these groups. In some embodiments, the first auxiliary ligand is:

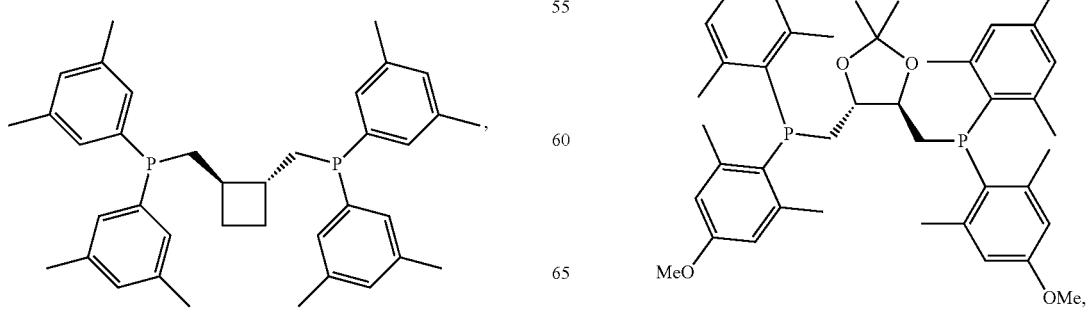

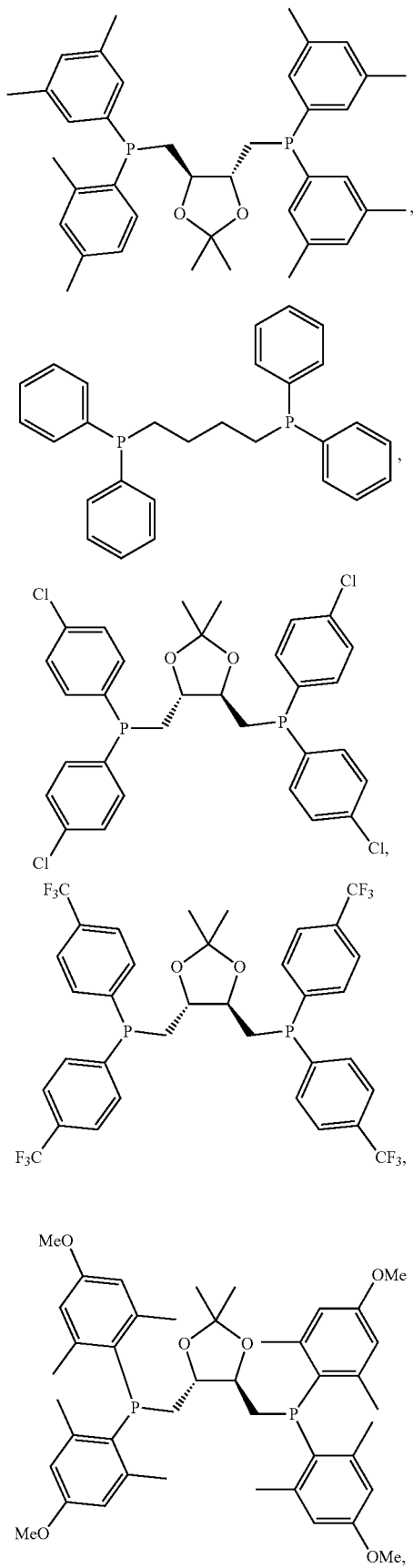

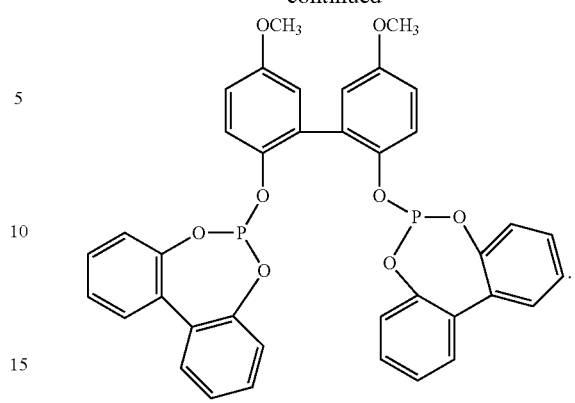

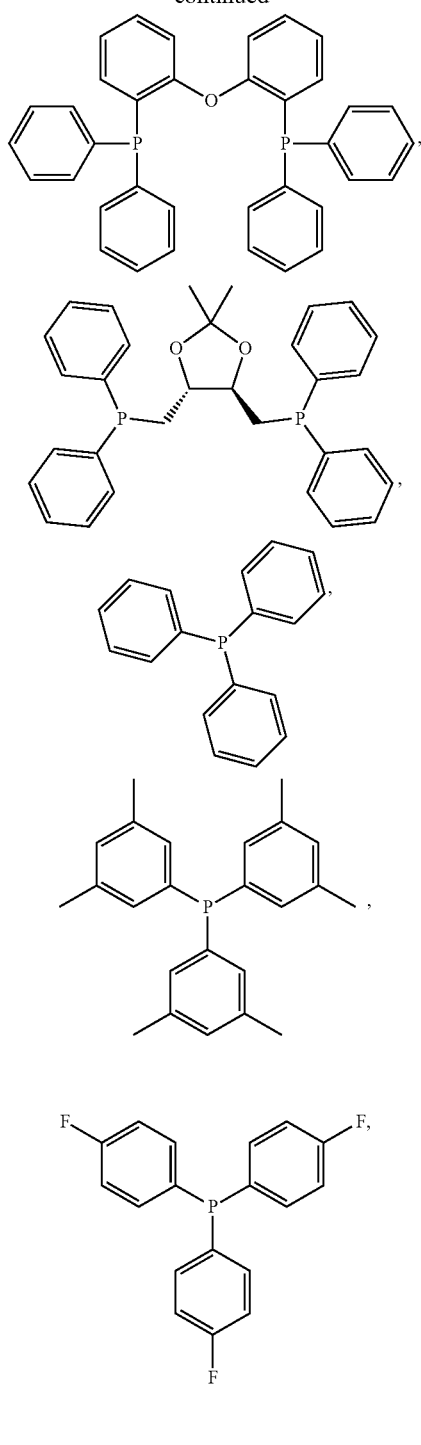

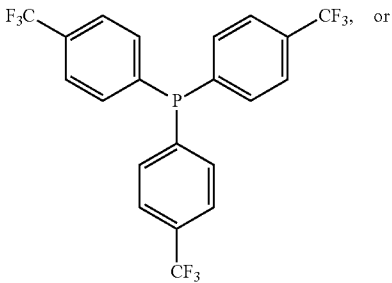

In some embodiments, the molar ratio of the rhodium complex to the first auxiliary ligand in the reaction mixture is from about 1:0.1 to about 1:100. In some embodiments, the molar ratio of the rhodium complex to the first auxiliary ligand in the reaction mixture is from about 1:1 to about 1:2. In some embodiments, the reaction mixture further comprises a second auxiliary ligand, wherein the second auxiliary ligand is a phosphine$_{(C \leq 30)}$, a diphosphine$_{(C \leq 50)}$, a phosphite$_{(C \leq 30)}$, a diphosphite$_{(C \leq 50)}$, or a substituted version of any of these groups. In some embodiments, the second auxiliary ligand is:

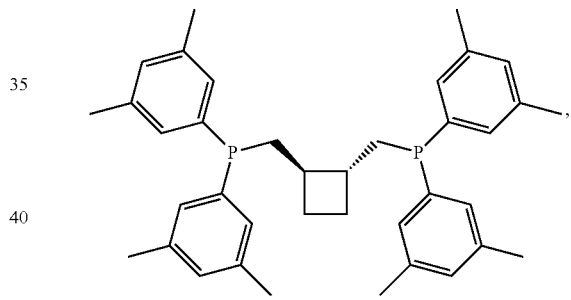

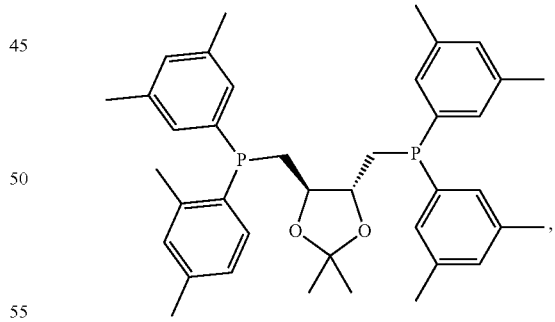

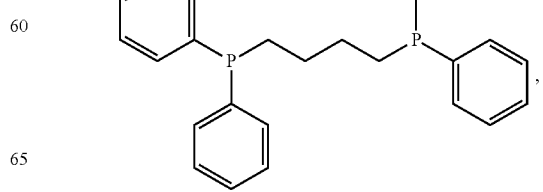

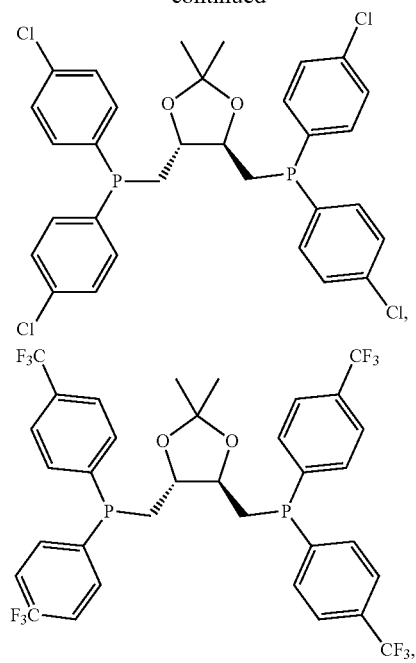

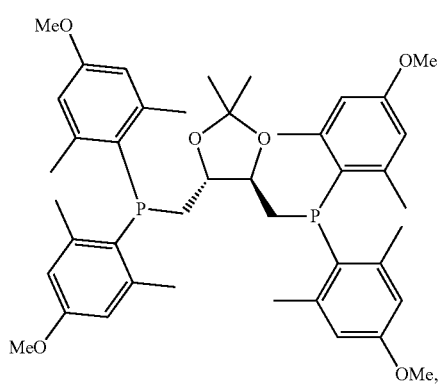

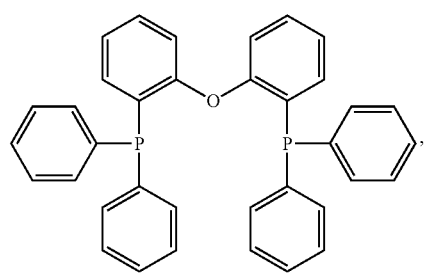

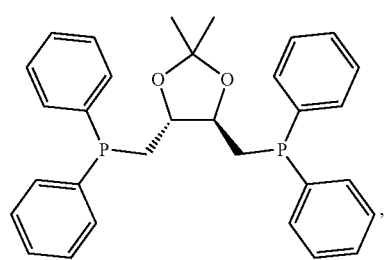

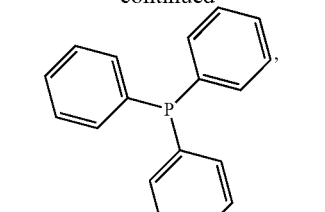

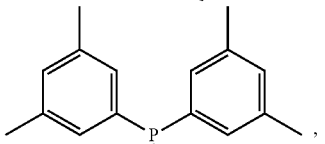

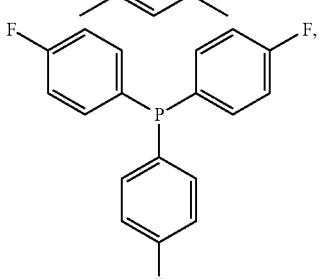

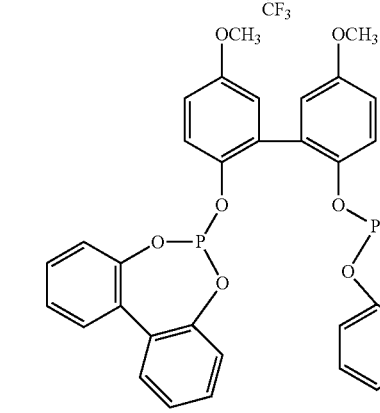

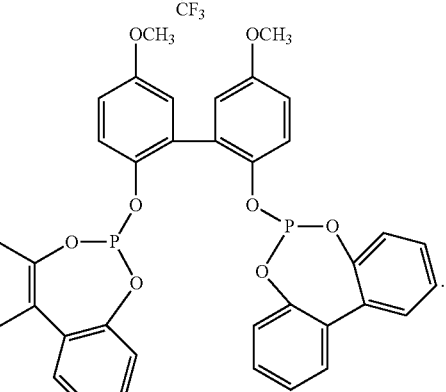

In some embodiments, the method further comprises adding a solvent to the reaction mixture. In some embodiments, the reacting step also makes a 2-methyl aldehyde$_{(C \leq 13)}$, wherein the ratio of aldehyde$_{(C \leq 13)}$ to the 2-methyl aldehyde$_{(C \leq 13)}$ made in the reacting step is at least 10:1. In some embodiments, the method further comprises heating the reaction mixture to a temperature from about 50° C. to about 110° C. In some embodiments, the reacting step is run at a H$_2$/CO pressure from about 40 psi to about 600 psi. In some embodiments, the ratio of H$_2$ to CO is approximately 1:1.

In yet another aspect, the present disclosure provides a method for the hydroformylation of a terminal alkene$_{(C\le12)}$ or a substituted terminal alkene$_{(C\le12)}$ in a reaction vessel to form an aldehyde$_{(C\le13)}$ or substituted aldehyde$_{(C\le13)}$ comprising the following steps in any order:
a) adding a rhodium complex to the reaction vessel;
b) adding an N-heterocyclic carbene to the reaction vessel;
c) adding the terminal alkene$_{(C\le12)}$ or the substituted terminal alkene$_{(C\le12)}$ to the reaction vessel;
d) adding a first auxiliary ligand to the reaction vessel;
e) pressurizing the reaction vessel with hydrogen ($H_2$) and carbon monoxide (CO); and
f) heating the reaction vessel to a temperature from about 50° C. to about 110° C.;

whereby the terminal alkene$_{(C\le12)}$ or the substituted terminal alkene$_{(C\le12)}$ reacts in the presence of a catalyst comprising the rhodium complex and the N-heterocyclic carbene with the $H_2$ and the CO under conditions sufficient to cause a reaction to form an aldehyde$_{(C\le13)}$ or a substituted aldehyde$_{(C\le13)}$. In some embodiments, the rhodium complex and the N-heterocyclic carbene are added to the reaction vessel in an approximately 1:1 ratio.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula does not mean that it cannot also belong to another generic formula.

DESCRIPTION OF ILLUSTRATIVE EMBODIMENTS

I. Hydroformylation of Allyl Alcohols Using (acac)(CO)Rh-Imes Catalyst

In one aspect of the present disclosure, there are provided methods of using homogenous rhodium catalysts comprising or in the presence of N-heterocyclic carbene ligands for the hydroformylation of olefins and substituted olefins, including for example, the use of (acac)(CO)Rh-Imes as a catalyst and/or pre-catalyst for the selective hydroformylation of allyl alcohol to 4-hydroxybutyraldehyde (HBA).

Imes represents a specific example of an N-heterocyclic carbene (NHC) ligand, which is a sub group of compounds known as persistent carbenes. Other NHC ligands, including, for example, other types of imidazol-2-ilidenes, may be used for the processes provided herein. Further examples of NHC ligands are provided by Gil and Trzeciak, 2011; Cesar, et. al, 2011; Nolan, et. al., 2009; Herrman, 2002; Chen; et al., 2005; Gil, et al., 2008; Bortenschlager, et. al., 2005; Datt, et al., 2005; and Bitterman; et al., 2008, all of which are incorporated herein by reference. In some embodiments of the present disclosure, the NHC ligand has a formula:

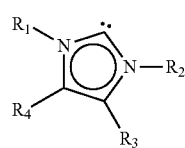
(I)

wherein: $R_1$ and $R_2$ are each independently alkyl$_{(C\le12)}$, aryl$_{(C\le42)}$, aralkyl$_{(C\le42)}$, or a substituted version of any of these groups; $R_3$ and $R_4$ are each independently hydrogen, halo, hydroxy, amino, or alkyl$_{(C\le12)}$, aryl$_{(C\le12)}$, aralkyl$_{(C\le12)}$, or a substituted version of any of these groups; or $R_3$ and $R_4$ are taken together and are alkanediyl$_{(C\le12)}$, alkenediyl$_{(C\le12)}$, or a substituted version of either of these groups.

In some embodiments, the rhodium catalyst was prepared by combining a rhodium complex with an N-heterocyclic carbene. One non-limiting examples of the complexes which can be prepared in the examples include (acac)(CO)Rh-Imes can be represented by the following structure formula:

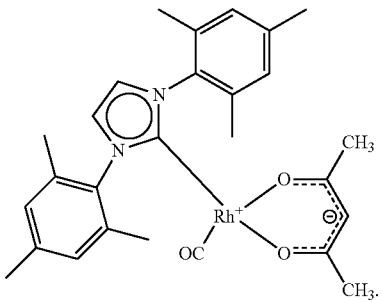

In the above-depicted complex, the "Imes" ligand corresponds to 1,3-bis(2,4,6-trimethyl)phenyl imidazol-2-ylidene, which has the formula:

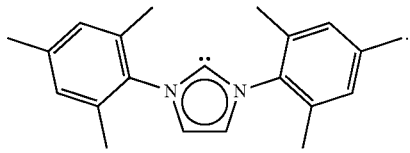

See Examples 1-3 below for additional details. In general, the compounds discussed in this disclosure, e.g., catalysis, pre-catalysts, complexes and ligands, can be prepared according to the methods described in the Examples section below. These methods can be further modified and optimized using the principles and techniques of inorganic and organic chemistry as applied by a person skilled in the art. Such principles and techniques are taught, for example, in *March's Advanced Organic Chemistry: Reactions, Mechanisms, and Structure* (2007) and *Advanced Inorganic Chemistry, Fifth Edition* (1988), which are both incorporated by reference herein.

In some embodiments, there are provided methods of hydroformylating a terminal alkene or substituted terminal alkene to produce an aldehyde or substituted aldehyde. For example, one such method comprises reacting allyl alcohol with carbon monoxide (CO) and hydrogen ($H_2$) in the presence of a catalyst of the formula:

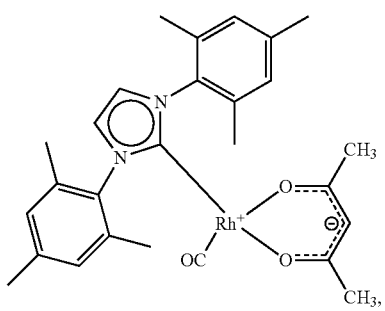

to make HBA.

In some embodiments, the reacting step also makes a 2-methyl aldehyde or a substituted 2-methyl aldehyde, wherein the ratio of the aldehyde to the 2-methyl aldehyde made in the reacting step is at least 10:1, preferably at least 15:1, more preferably at least 17:1, most preferably at least 18:1.

In some methods the methods further comprise the step of admixing a rhodium complex to a solvent to form a catalyst-precursor solution. In some embodiments, the rhodium complex is a rhodium(I) complex. In some embodiments, the solvent is an alkane$_{(C \leq 20)}$, an arene$_{(C \leq 20)}$, an alcohol$_{(C \leq 20)}$, an ether$_{(C \leq 20)}$, or a mixture thereof, for example, toluene, cyclohexane, methyl t-butyl ether, isopropanol, or a mixture thereof.

In some embodiments, the methods further comprise a step of admixing the NHC to the rhodium complex solution to form a catalyst solution comprising the NHC and rhodium catalyst. In other embodiments, the addition of the NHC and the rhodium complex to the solvent is reversed. In some embodiments, the methods further comprise a step of admixing the terminal alkene or substituted terminal alkene, the carbon monoxide, and the hydrogen to the catalyst solution to form a reaction mixture.

In some embodiments, the methods further comprise heating the catalyst-precursor solution, the catalyst solution, or the reaction mixture, to from about 50° C. to about 110° C., or preferably to from about 60° C. to about 95° C. In some embodiments, the methods further comprise running the reaction steps at a pressure from about 40 psi to about 600 psi, preferably from about 100 psi to about 300 psi, more preferably from about 120 to about 200 psi.

In some embodiments, less than about 1% by weight $C_3$ product is made in the reacting step, wherein $C_3$ product consists of n-propanol and propionaldehyde.

In some embodiments, the methods further comprise a step of admixing an auxiliary ligand, such as a phosphine, a diphosphine, a phosphite, a diphosphite, or a substituted version of any of these groups, into the reaction mixture. In some embodiments, the molar ratio of catalyst to the auxiliary ligand is from about 1:0.1 to about 1:100. In some of these embodiments, it is from about 1:2 to about 1:3. In some embodiments, the phosphine, the diphosphine, the phosphite, or the diphosphate is a compound described in Table 17. In some embodiments, the methods further comprise a step of admixing a second auxiliary ligand, for example, a phosphine, a diphosphine, a phosphite, a diphosphite, or a substituted version of any of these groups, into the reaction mixture. In some of these embodiments, the first auxiliary ligand is triphenylphosphine and the second auxiliary ligand is trans-1,2-bis[di(3,5-dimethylphenyl)phosphine-methyl]cyclobutane.

The compounds described in this disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. For example, the catalysts and ligands may occur as racemates and racemic mixtures, single enantiomers, diastereomeric mixtures and individual diastereomers. In some embodiments, a single diastereomer is obtained. The chiral centers of the present disclosure can have the S or the R configuration.

In addition, atoms making up the ligands and catalysts of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In another aspect, the present disclosure provides methods for preparing 4-hydroxybutyraldehdye from allyl alcohol, $H_2$, and carbon monoxide in the presence of a homogeneous Rh-based catalyst and an N-heterocyclic carbene ligand, such as Imes. In some embodiments, such methods consist of adding an auxiliary ligand such as a phosphine, a diphosphine, a phosphite, a diphosphite ligand to a solvent. In some embodiments, the solvent is an aliphatic or aromatic hydrocarbon, an alcohol, an ether, or a mixture of such solvents. In some embodiments, the ratio of the auxiliary ligand to Rh catalyst is from about 0.1:1 to about 100:1 ligand to catalyst. In some embodiments, the ratio of ligand to Rh catalyst is from about 1:1 to about 2:1 ligand to catalyst.

In some embodiments, the reaction vessel is flushed with a mixture of hydrogen ($H_2$) and carbon monoxide (CO) gas. In some embodiments, this flushing is performed 1 to 5 times. For example, in some embodiments, the reaction vessel is flushed 3 times with a mixture of hydrogen and carbon monoxide. In some embodiments, the ratio of hydrogen to carbon monoxide gas in the gas phase is from about 100:1 to about 1:4, more preferably from about 10:1 and 1:2, and most preferably the ratio is 1:1. In some embodiments, the ratio of hydrogen to carbon monoxide gas varies between the liquid and gas phase. In some embodiments, the ratio of hydrogen to carbon monoxide in the liquid phase is from about 10:1 to about 1:2, from about 5:1 to about 1:2, or 1:1.

In some embodiments, the reaction vessel is pressurized with the hydrogen and carbon monoxide gas mixture from about 100 psig to about 250 psig. In some of these embodiments, the reaction vessel is pressurized from about 120 psig to about 200 psig. In some embodiments, the reaction vessel may be heated to a temperature form about 50° C. to about 120° C. In some of these embodiments, the temperature is heated to a temperature from about 65° C. to about 95° C. For example, the temperature of the reaction vessel may be set at 65, 75, 85, or 95° C. In some embodiments, once the temperature has been reached, the reaction vessel is allowed to sit for a period of time, for example, from about 1 minute to about 60 minutes. In some of these embodiments, this waiting period is about 5 minutes. In some embodiments, the allyl alcohol may be added via injection to the reaction mixture. In other embodiments, the allyl alcohol is added to the reaction through other methods, as would be known to those of skill in the art. In some embodiments, the pressure in the reaction vessel is increased to a pressure from about 175 to about 300 psig, for example, 200 psig. In some embodiments, the reaction is kept at an approximately constant pressure. In some embodiments, the uptake rate of additional hydrogen ($H_2$) and/or carbon monoxide (CO) gas may be used to measure the completion of the reaction. In some embodiments, for example, when the reaction no longer uptakes additional $H_2$ and/or CO or the uptake rate is reduced, the reaction vessel is cooled and/or depressurized. In some embodiments, for example, after depressurization and/or cooling, the reaction mixture is analyzed, for example, via gas chromatography to determine the ratio of different products produced. General methods for the hydroformylation of allyl alcohol are taught, for example, in U.S. Pat. No. 7,294,602, which is incorporated herein by reference.

II. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

III. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2H$); "halo" means independently —F, —Cl, —Br or —I; "nitro" means —$NO_2$; "cyano" means —CN; and "amino" means —$NH_2$. Any undefined valency on an atom of a structure shown in this application implicitly represents a hydrogen atom bonded to that atom.

In the context of chemical formulas, the symbol "—" means a single bond, "=" means a double bond, and "≡" means triple bond. The symbol "----" represents an optional bond, which if present is either single or double. The symbol "⚌" represents a single bond or a double bond. Thus, for example, the formula

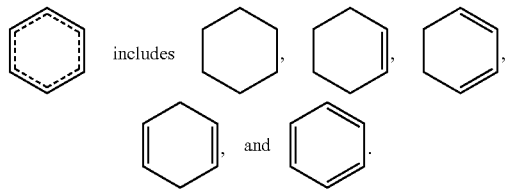

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "∼∼∼", when drawn perpendicularly across a bond

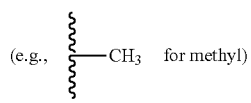

indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⊶⊷⊷⊷" means a single bond where the group attached to the thick end of the wedge is "into the page". The symbol "∼∼∼" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M—C, M=C, M----C, and M⚌C, each refers to a bond of any type and order between a metal atom and a carbon atom.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkanes/alkenyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —$CH_3$ (Me), —$CH_2CH_3$ (Et), —$CH_2CH_2CH_3$ (n-Pr or propyl), —$CH(CH_3)_2$ (i-Pr, $^i$Pr or isopropyl), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl, t-butyl, t-Bu or $^t$Bu), —$CH_2C(CH_3)_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. It is noted that while the alkanediyl group is aliphatic, once connected at both ends, this group is not precluded from forming an aromatic structure. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, —CH=CHCH=CH$_2$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

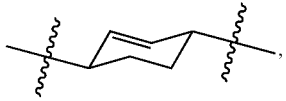 [SMILES: *C1C=CC(*)CC1]

are non-limiting examples of alkenediyl groups. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, -C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

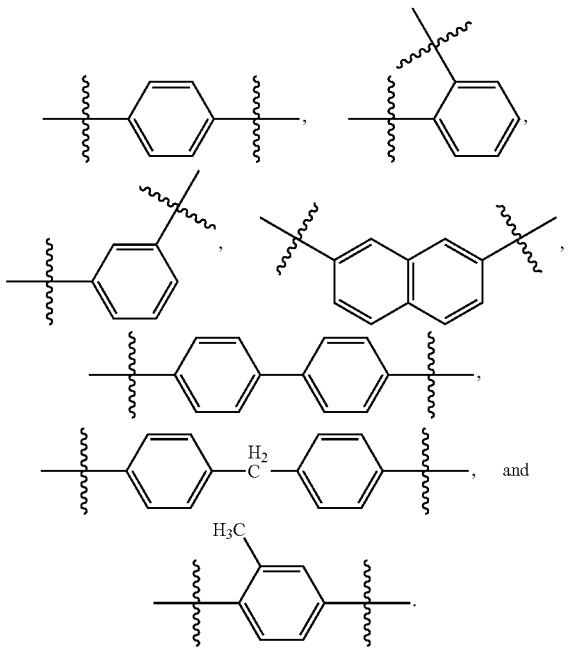

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl or -alkanediyl—CH-(aryl)$_2$, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

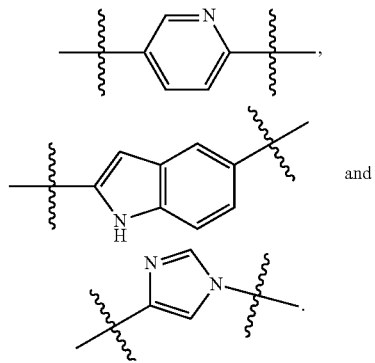

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, 'NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

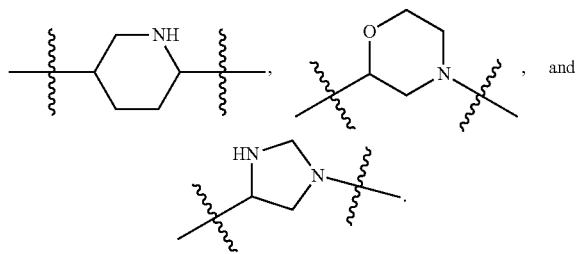

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl—O—, or -alkanediyl—O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl—NH—, or -alkanediyl—NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "phosphine" when used without the "substituted" modifier refers to a compound of the formula PR$_3$, wherein each R is independently hydrogen, alkyl, alkenyl, aryl, and aralkyl, as those terms are defined above. Non-limiting examples of phosphines include $PMe_3$ and $PPh_3$. The term "alkylphosphine" is a subset of phosphine, wherein each R is an alkyl group. Similarly, the term "arylphosphine" is a subset of phosphine, wherein each R is an aryl group. The term "diphosphine" when used without the "substituted" modifier refers to a compound of the formula $R_2$-P-L-P-$R_2$, wherein each R is independently hydrogen, alkyl, alkenyl, aryl, and aralkyl, as those terms are defined above, and wherein L is alkanediyl, alkenediyl, alkynediyl, arenediyl, heteroarenediyl, heterocycloalkanediyl, -arenediyl-O-arenediyl-, —$CH_2$-arenediyl—$CH_2$—, or one of the following groups:

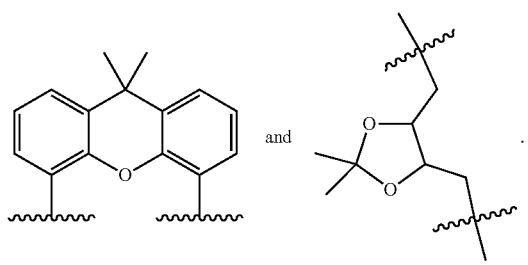 [SMILES: *c1cccc2c1Oc1c(*)cccc1C2(C)C ; *CC1OC(C)(C)OC1C*]

When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$. Non-limiting examples of diphosphines include:

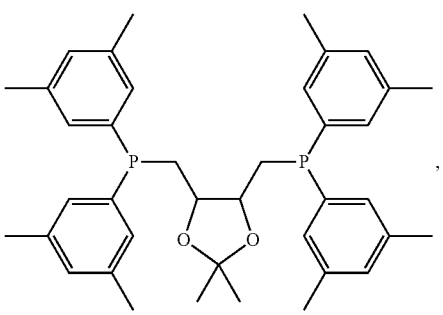

,

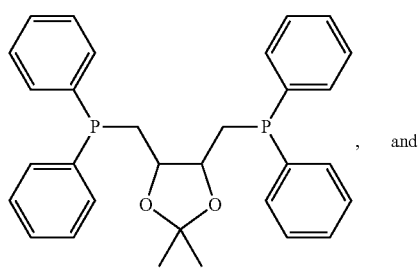

, and

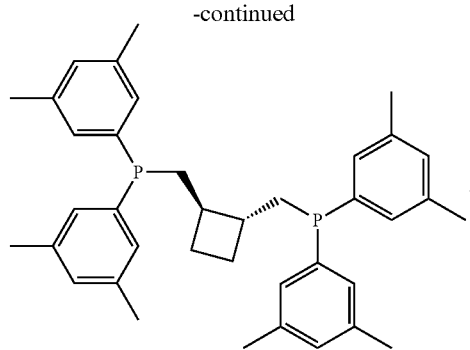

The term "phosphite" when used without the "substituted" modifier refers to a compound of the formula $PR_3$, wherein each R is independently alkoxy, aryloxy, and aralkoxy, as those terms are defined above. Non-limiting examples of phosphites include $P(OMe)_3$ and $P(OPh)_3$. The term "alkylphosphite" is a subset of phosphite, wherein each R is an alkoxy group. Similarly, the term "arylphosphite" is a subset of phosphite, wherein each R is an aryloxy group. The term "diphosphite" when used without the "substituted" modifier refers to a compound of the formula $R_2$-P-L-P-$R_2$, wherein each R is independently alkoxy, aryloxy, and aralkoxy, as those terms are defined above, and wherein L is alkoxydiyl or aryloxydiyl. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$. Non-limiting examples of diphosphites include:

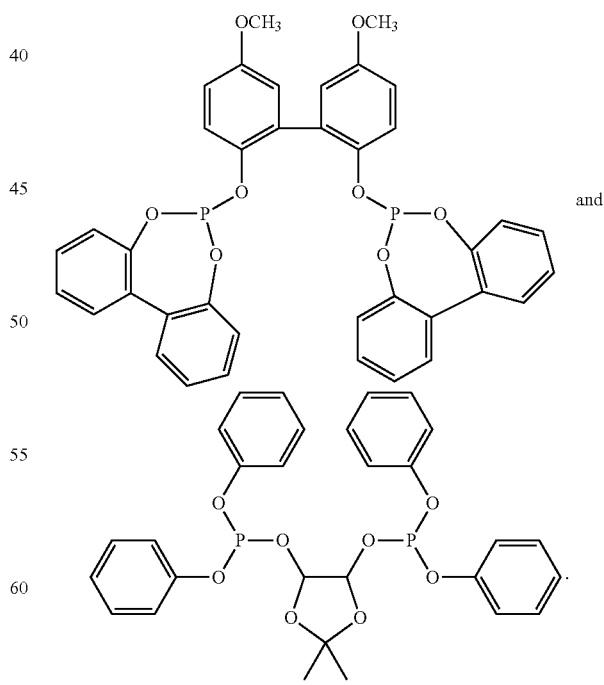

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

An "isomer" of a first compound is a separate compound in which each molecule contains the same constituent atoms as the first compound, but where the configuration of those atoms in three dimensions differs.

A "method" is series of one or more steps undertaking lead to a final product, result or outcome. As used herein, the word "method" is used interchangeably with the word "process".

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

IV. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Generation of Rhodium NHC Catalysts

Catalyst 1: Generation of (acac)(CO)Rh-IMes Catalyst

The (acac)(CO)Rh-Imes catalyst was prepared by combining Rh(acac)(CO)$_2$ with the free IMes ligand, in a variation of the method employed by Datt, et al., 2005, which is incorporated herein by reference. The (acac)(CO)Rh-IMes catalyst was prepared on Schlenk line, in a chloride-free environment by combining Rh(acac)(CO)$_2$ with the free IMes ligand in anhydrous toluene instead of THF. Rh(acac)(CO)$_2$ (Strem Chemical, 99%) 0.415 g, 1.61 mmol was dissolved in approximately 30 mL anhydrous toluene to give a yellow solution. A vial of free Imes (Strem Chemical, 98%) 0.5 g, 1.64 mmol was added to the solution under a strong downward stream of argon from an inverted conical funnel clamped over the open flask to provide an inert atmosphere. The septum was replaced and the deep brownish yellow solution for 1.5 hours. The solvent was removed in vacuo and the residue washed twice with pentane then dried in vacuo. The residue was dissolved in methylene chloride, filtered and the solvent removed under vacuum. The residue was triturated and washed with pentane which was decanted and the process repeated twice more to give a yellow powder. The powder was dried in vacuo for 12 hours, isolated and after characterization by NMR used and handled in open air.

Scheme 1:
Preparation of (acac)(CO)RhImes from free IMes and Rh(acac)(CO)$_2$

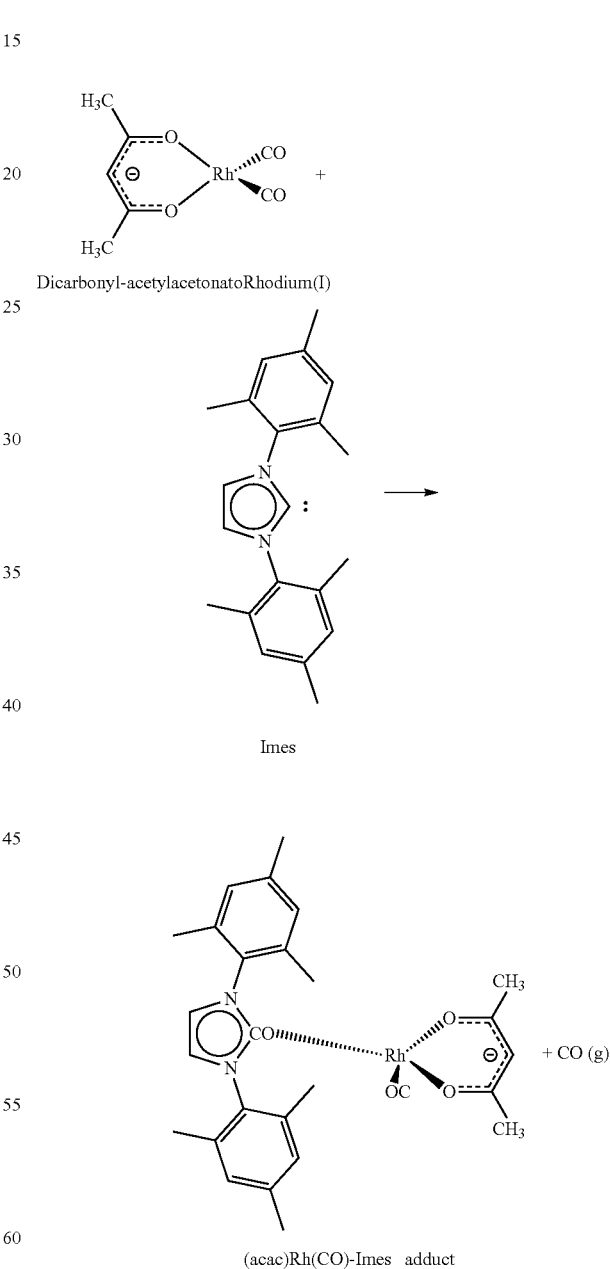

Dicarbonyl-acetylacetonatoRhodium(I)

Imes (acac)Rh(CO)-Imes adduct

The corresponding (acac)Rh(CO)—NHC complexes of other free carbene ligands were prepared following the same procedure as shown in catalysts 2 to 4 and the ligand structures are shown in Table 1.

TABLE 1

Structures of the free NHC ligands of Catalysts 1-6.

| NHC Structure | Abbreviation | IUPAC Name |
|---|---|---|
| | IMes | 1,3-Bis(2,4,6-trimethylphenyl)imidazol-2-ylidene |
| | IPr | 1,3-Bis(2,6-di-i-propylphenyl)imidazol-2-ylidene |
| | ItBu | 1,3-Di-t-butylimidazol-2-ylidene |
| (structure with MeO, Ph groups) | IPr*OMe | N,N'-Bis(2,6-bis(diphenylmethyl)-4-methoxyphenyl)imidazol-2-ylidene |
| (benzimidazole structure with t-Bu groups) | BItBu | 1,3-Di-t-butylbenzimidazol-2-ylidene |
| (structure with two p-Cl-phenyl groups) | I(p-Cl-Ph)Mes | 1,3-Bis(4-chlorophenyl)imidazol-2-ylidene |

Catalyst 2: Generation of (acac)(CO)Rh-IPr Catalyst

The (acac)(CO)Rh-IPr catalyst was prepared in the same manner as the (acac)(CO)Rh-IMes catalyst (Catalyst 1), substituting free IPr (Strem Chemical, 98%), 0.25 g, 0.643 mmol for free IMes. Rh(acac)(CO)$_2$ (Strem Chemical, 99%) 0.166 g, 0.643 mmol was used.

Catalyst 3: Generation of (acac)(CO)Rh-ItBu Catalyst

The (acac)(CO)Rh-ItBu catalyst was prepared in the same manner as the (acac)(CO)Rh-IMes catalyst (Catalyst 1), substituting free ItBu (Strem Chemical, 98%), 0.25 g, 1.39 mmol for free IMes. Rh(acac)(CO)$_2$ (Strem Chemical, 99%) 0.35 g, 1.36 mmol was used.

Catalyst 4: Generation of (acac)(CO)Rh-IPr*OMe Catalyst

The (acac)(CO)Rh-IPr*OMe catalyst was prepared in the same manner as the (acac)(CO)Rh-IMes catalyst (Catalyst 1), substituting free IPr*OMe (Strem Chemical, 98%), 0.25 g, 0.264 mmol for free IMes. Rh(acac)(CO)$_2$ (Strem Chemical, 99%) 0.065 g, 0.252 mmol was used.

Example 2

Generation of (acac)(CO)Rh-NHC Catalysts via Deprotonation of Imidazolium or Benzimidazolium Salts

Catalyst 5: Generation of (acac)(CO)Rh-BItBu Catalyst

The (acac)(CO)Rh-BItBu catalyst was prepared in two steps: deprotonation of BItBu.HCl followed by reaction with Rh acac as in the preceding examples without isolating the ligand. Free BItBu was generated by deprotonation of BItBu.HCl with 0.5 M sodium methoxide solution in methanol. 1,3-Di-t-butylbenzimidazolium chloride (Strem Chemical, 97%) (BItBu.HCl) 0.5 g, 1.87 mmol was charged into a 100 mL Schlenk flask and the flask evacuated and refilled with argon twice then kept under argon. A methanol solution of sodium methoxide (Sigma Aldrich, 0.5 M) 3.75 ml, 1.87 mmol, was injected into the flask via syringe and needle under an argon atmosphere. A dark reddish/brown mixture formed as the benzimidazolium salt dissolved upon deprotonation. The mixture was stirred for an hour then the methanol was evaporated off under vacuum. The reddish oily residue was dried in vacuo for a further 1 and ½ hours. A solution of Rh(acac)(CO)$_2$ (Strem Chemical, 99%) 0.461 g, 1.78 mmol was dissolved in approximately 30 mL anhydrous toluene to give a yellow solution which was transferred via cannula into the flask containing the deprotonated BItBu ligand to give a deep brownish solution. The solution was stirred for 1.5 hours then the toluene removed in vacuo. The residue was washed with pentane twice and the pentane decanted each time. Fresh toluene (10 mL) was added to the residue then the mixture drawn into a syringe and filtered a through a 0.1 micron Whatman Puradisc™ disposable filter device to remove the generated salt and give a brownish-yellow solution. The toluene was removed in vacuo. The residue was triturated and washed with pentane which was decanted and the process repeated once more to give a yellow powder which was dried in vacuo overnight for ~12 hours. Purity of the product obtained was confirmed by NMR and the material handled and used in open air.

Catalyst 6: Generation of (acac)(CO)Rh-I(p-Cl-Ph) Catalyst

The (acac)(CO)Rh-I(p-Cl-Ph) was prepared following the same procedure as in Catalyst 5. Free I(p-Cl-Ph) was generated by deprotonation Ip-ClPh.HCl with 0.5 M sodium methoxide solution in methanol. 1,3-Bis(4-chlorophenyl) imidazolium chloride (Strem Chemical, 97%) 0.25 g, 0.768 mmol was deprotonated with sodium methoxide (Sigma Aldrich, 0.5 M) 1.6 ml, 0.795 mmol. As in Catalyst 5, a solution of Rh(acac)(CO)$_2$ (Strem Chemical, 0.18 g, 0.698 mmol) was added to prepare the catalyst which was isolated and characterized in a similar manner.

Example 3

Catalytic Hydroformylation of Terminal Alkenes

The standard hydroformylation experiment was carried out in anhydrous toluene with the stoichiometry determined by the amount of Rh. In a typical experiment, a rhodium complex (1 equivalent, 4.3×10$^{-5}$ moles) was added to this solution of dry gassed toluene (15 g) and one or more phosphine ligands. This solution was then transferred to a 50 mL Parr autoclave. The autoclave was then flushed three times with a 1:1 CO/H$_2$ mixture, and pressurized to 180 psig, and the autoclave heated with stirring to the indicated temperature, for example 65° C. Once the desired temperature was stably attained for at least 5 minutes, allyl alcohol (3.5 mL) was then injected and the autoclave pressure increased to 200 psig with the CO:H$_2$ gas mixture. The reactor was then maintained at a constant 200 psig pressure and the gas uptake with time was monitored until there was no further gas uptake. The reactor was cooled down, depressurized and the solution was analyzed by gas chromatography to determine the products of the reaction, typically HBA, MHPA and C$_3$ products, (n-propanol and propionaldehyde). The above reactions were used for the reactions in Tables 2-12. In high temperature reactions described in Tables 13 and 14, similar reaction conditions were utilized but with a temperature of 85° C. rather than 65° C. Similar reaction conditions can also be used to hydroformylated other terminal alkenes such as 1-octene as described in Tables 15 and 16.

TABLE 2

Comparison Examples with No Carbene

| Sample ID | Rh Source 4.3e−5 Moles | Ligand 1: Diphosphine 8.6e−5 Moles | Ligand 3: Monophosphine 4.3e−5 Moles |
|---|---|---|---|
| C1 | Rh(CO)$_2$acac | Gen4 | |
| C2 | Rh(CO)$_2$acac | | TPP |
| C3 | Rh(CO)$_2$acac | DPPB | |
| C4 | Rh(CO)$_2$acac | DPEPhos | |
| C5 | Rh(CO)$_2$acac | DIOP | |
| C6 | Rh(CO)$_2$acac | Cl-DIOP | |
| C7 | Rh(CO)$_2$acac | CF$_3$-DIOP | |
| C8 | Rh(CO)$_2$acac | Gen3 | |
| C9 | Rh(CO)$_2$acac | Mod-DIOP | |
| C10 | Rh(CO)$_2$acac | BIPHEPHOS | |

| Sample ID | HBA mol % | HMPA mol % | C3 mol % | L:B Ratio mol % | AA Conv % |
|---|---|---|---|---|---|
| C1 | 90.6 | 8.4 | 0.44 | 10.8 | 99.66 |
| C2 | 59.6 | 38.3 | 0.34 | 1.56 | 99.91 |
| C3 | 70.4 | 26.2 | 0.89 | 2.69 | 98.75 |
| C4 | 73.27 | 11.38 | 0.48 | 6.43 | 85.13 |
| C5 | 86.37 | 12.67 | 0.15 | 7.4 | 99.19 |
| C6 | 79.82 | 19.44 | 0.38 | 4.11 | 99.94 |
| C7 | 76.19 | 21.19 | 2.54 | 3.91 | 99.92 |
| C8 | 88.9 | 10.2 | 0.42 | 8.75 | 99.85 |
| C9 | 82.18 | 14.73 | 0.28 | 5.58 | 99.94 |
| C10 | 88.3 | 9.8 | 0.93 | 9.04 | 99.99 |

TABLE 3

Comparison Examples with No Carbene Reaction Conditions

| Sample ID | Rh Source | Mass (g) | Mols ×10$^{-5}$ | Phosphine | Mass (g) | Mols ×10$^{-5}$ |
|---|---|---|---|---|---|---|
| C1 | Rh(acac)(CO)$_2$ | 0.0110 | 4.3 | Gen4 | 0.0489 | 8.6 |
| C2 | Rh(acac)(CO)$_2$ | 0.0111 | 4.3 | TPP | 0.0338 | 12.9 |
| C3 | Rh(acac)(CO)$_2$ | 0.0110 | 4.3 | DPPB | 0.0366 | 8.6 |
| C4 | Rh(acac)(CO)$_2$ | 0.0111 | 4.3 | DPEPhos | 0.0464 | 8.6 |
| C5 | Rh(acac)(CO)$_2$ | 0.0111 | 4.3 | DIOP | 0.0429 | 8.6 |
| C6 | Rh(acac)(CO)$_2$ | 0.0111 | 4.3 | Cl-DIOP | 0.0546 | 8.6 |
| C7 | Rh(acac)(CO)$_2$ | 0.0112 | 4.3 | CF$_3$-DIOP | 0.0892 | 8.6 |
| C8 | Rh(acac)(CO)$_2$ | 0.0112 | 4.3 | Gen3 | 0.0518 | 8.6 |
| C9 | Rh(acac)(CO)$_2$ | 0.0111 | 4.3 | Mod-DIOP | 0.0629 | 8.6 |
| C10 | Rh(acac)(CO)$_2$ | 0.0112 | 4.3 | BIPHEPHOS | 0.0717 | 8.6 |

TABLE 4

Examples with Only Carbene

| Sample ID | Rh Source 4.3e−5 Moles | HBA mol % | HMPA mol % | C3 mol % | L:B Ratio mol % | AA Conv % |
|---|---|---|---|---|---|---|
| E1 | (IMes)Rh(acac)(CO) | 6.01 | 11.27 | 0.89 | 0.53 | 18 |

TABLE 5

Examples with Carbene and Generation 4 Diphosphine Catalyst

| Sample ID | Rh Source 4.3e-5 Moles | Ligand 1: Diphosphine 8.6e-5 Moles | Ligand 2: Carbene 4.3e-5 Moles | Ligand 3: Monophosphine 4.3e-5 Moles |
|---|---|---|---|---|
| E2 | (IMes)Rh(acac)(CO) | Gen4 | | |
| E3 | (IMes)Rh(acac)(CO) | Gen4 | | TPP |
| E4 | (IPr)Rh(acac)(CO) | Gen4 | | |
| E5 | (ItBu)Rh(acac)(CO) | Gen4 | | |
| E6 | (BItBu)Rh(acac)(CO) | Gen4 | | |
| E7 | (Ipr*OMe)Rh(acac)(CO) | Gen4 | | |

| Sample ID | HBA mol % | HMPA mol % | C3 mol % | L:B Ratio mol % | AA Conv % |
|---|---|---|---|---|---|
| E2 | 18.3 | 0.5 | 0.59 | 33.58 | 19.47 |
| E3 | 20.1 | 0.4 | 1.01 | 47.78 | 22.71 |
| E4 | 41.4 | 2.2 | 0.91 | 18.44 | 45.84 |
| E5 | 10.1 | 0 | 0.86 | >100 | 10.93 |
| E6 | 90.5 | 7.1 | 0.65 | 12.8 | 99.13 |
| E7 | 87.4 | 7.2 | 0.68 | 12.16 | 95.64 |

TABLE 6

Examples with Carbene and Generation 4 Diphosphine Catalyst Reaction Conditions

| Sample ID | Rh Source | Mass (g) | Moles ×10$^{-5}$ | Diphosphine | Mass (g) | Moles ×10$^{-5}$ | Mono-phosphine | Mass (g) | Moles ×10$^{-5}$ |
|---|---|---|---|---|---|---|---|---|---|
| E2 | (IMes)Rh(acac)(CO) | 0.0231 | 4.3 | Gen4 | 0.0488 | 8.6 | | | |
| E3 | (IMes)Rh(acac)(CO) | 0.0229 | 4.3 | Gen4 | 0.0485 | 8.6 | TPP | 0.0334 | 12.9 |
| E4 | (IPr)Rh(acac)(CO) | 0.0262 | 4.3 | Gen4 | 0.0489 | 8.6 | | | |
| E5 | (ItBu)Rh(acac)(CO) | 0.0177 | 4.3 | Gen4 | 0.0488 | 8.6 | | | |
| E6 | (BItBu)Rh(acac)(CO) | 0.0201 | 4.3 | Gen4 | 0.0486 | 8.6 | | | |
| E7 | (Ipr*OMc)Rh(acac)(CO) | 0.0506 | 4.3 | Gen4 | 0.0489 | 8.6 | | | |

TABLE 7

Examples with Carbene and Additional Monodentate Phosphine

| Sample ID | Rh Source 4.3e−5 Moles | Ligand Monophosphine 4.3e−5 Moles | HBA mol % | HMPA mol % | C3 mol % | L:B Ratio mol % | AA Conv % |
|---|---|---|---|---|---|---|---|
| E8 | (IMes)Rh(acac)(CO) | TPP | 56 | 26.3 | 1.47 | 2.13 | 84.12 |
| E9 | (IMes)Rh(acac)(CO) | TXP | 14.6 | 2 | 1.14 | 7.13 | 17.73 |
| E10 | (IMes)Rh(acac)(CO) | T-pF-PP | 41.1 | 14 | 0.7 | 2.94 | 56.73 |
| E11 | (IMes)Rh(acac)(CO) | T-CF$_3$-PP | 84.8 | 12.2 | 0.75 | 6.93 | 99.51 |

TABLE 8

Examples with Carbene and Additional Monodentate Phosphine Reaction Conditions

| Sample ID | Rh Source | Mass (g) | Moles ×10$^{-5}$ | Mono Phosphine | Mass (g) | Moles ×10$^{-5}$ |
|---|---|---|---|---|---|---|
| E8 | (IMes)Rh(acac)(CO) | 0.0231 | 4.3 | TPP | 0.0340 | 12.9 |
| E9 | (IMes)Rh(acac)(CO) | 0.0231 | 4.3 | TXP | 0.0448 | 12.9 |
| E10 | (IMes)Rh(acac)(CO) | 0.0226 | 4.3 | T-pF-PP | 0.0409 | 12.9 |
| E11 | (IMes)Rh(acac)(CO) | 0.0230 | 4.3 | T-CF3-PP | 0.0889 | 12.9 |

TABLE 9

Examples with Carbene and Additional Bidenate Phosphine

| Sample ID | Rh Source 4.3e−5 Moles | Ligand 1: Diphosphine 8.6e−5 Moles | HBA mol % | HMPA mol % | C3 mol % | L:B Ratio mol % | AA Conv % |
|---|---|---|---|---|---|---|---|
| E12 | (IMes)Rh(acac)(CO) | DPPB | 9.3 | 1.1 | 1.11 | 8.33 | 11.48 |
| E13 | (IMes)Rh(acac)(CO) | DPEPhos | 42.2 | 5.1 | 1.4 | 8.28 | 48.88 |
| E14 | (IMes)Rh(acac)(CO) | DIOP | 21.1 | 0.9 | 0.2 | 23.99 | 23.2 |
| E15 | (IMes)Rh(acac)(CO) | Cl-DIOP | 27.1 | 1.8 | 0.75 | 14.66 | 29.66 |
| E16 | (IMes)Rh(acac)(CO) | $CF_3$-DIOP | 84.7 | 14.3 | 0.4 | 5.91 | 99.82 |
| E17 | (IMes)Rh(acac)(CO) | Gen3 | 18 | 0.7 | 0.17 | 27.13 | 18.82 |
| E18 | (IMes)Rh(acac)(CO) | Mod-DIOP | 18.3 | 1.3 | 0.6 | 14.46 | 20.71 |

TABLE 10

Examples with Carbene and Additional Bidenate Phosphine Reaction Condition

| Sample ID | Rh Source | Mass (g) | Moles ×10⁻⁵ | Diphosphine | Mass (g) | Moles ×10⁻⁵ |
|---|---|---|---|---|---|---|
| E12 | (IMes)Rh(acac)(CO) | 0.0229 | 4.3 | DPPB | 0.0364 | 8.6 |
| E13 | (IMes)Rh(acac)(CO) | 0.0230 | 4.3 | DPEPhos | 0.0459 | 8.6 |
| E14 | (IMes)Rh(acac)(CO) | 0.0231 | 4.3 | DIOP | 0.0426 | 8.6 |
| E15 | (IMes)Rh(acac)(CO) | 0.0228 | 4.3 | Cl-DIOP | 0.0543 | 8.6 |
| E16 | (IMes)Rh(acac)(CO) | 0.0230 | 4.3 | CF3-DIOP | 0.0892 | 8.6 |
| E17 | (IMes)Rh(acac)(CO) | 0.0231 | 4.3 | Gen3 | 0.0522 | 8.6 |
| E18 | (IMes)Rh(acac)(CO) | 0.0228 | 4.3 | Mod-DIOP | 0.0374 | 8.6 |

TABLE 11

Examples with Carbene and Additional Bidenate Phosphine

| Sample ID | Rh Source 4.3e−5 Moles | Ligand 1: Diphosphine 8.6e−5 Moles | HBA mol % | HMPA mol % | C3 mol % | L:B Ratio mol % | AA Conv % |
|---|---|---|---|---|---|---|---|
| E19 | (IMes)Rh(acac)(CO) | BIPHEPHOS | 90.9 | 7.3 | 1.17 | 12.52 | 100 |
| E20 | (I(p-Cl—Ph))Rh(acac)(CO) | BIPHEPHOS | 90.6 | 8.1 | 1.01 | 11.13 | 99.96 |

TABLE 12

Examples with Carbene and Additional Bidenate Phosphite Reaction Conditions

| Sample ID | Rh Source | Mass (g) | Moles ×10⁻⁵ | Diphosphine | Mass (g) | Moles ×10⁻⁵ |
|---|---|---|---|---|---|---|
| E19 | (IMes)Rh(acac)(CO) | 0.0233 | 4.3 | BIPHEPHOS | 0.0713 | 8.6 |
| E20 | (I(p-Cl—Ph)Rh(acac)(CO) | 0.0227 | 4.3 | BIPHEPHOS | 0.0712 | 8.6 |

TABLE 13

Examples with Carbene and Additional Phosphine at High Temperatures

| Sample ID | Rh Source 4.3e−5 Moles | Ligand 1: Diphosphite 8.6e−5 Moles | Ligand 2: Carbene 4.3e−5 Moles | Ligand 3: Monophosphine 4.3e−5 Moles |
|---|---|---|---|---|
| E21 | Rh(CO)2acac | Gen4 | IMes (added in-situ) | |
| E22 | (IMes)Rh(acac)(CO) | Gen4 | | |
| E23 | (IMes)Rh(acac)(CO) | Gen3 | | |
| E24 | (IMes)Rh(acac)(CO) | DIOP | | |
| E25 | (IMes)Rh(acac)(CO) | Gen4 | | TPP |

| Sample ID | HBA mol % | HMPA mol % | C3 mol % | L:B Ratio mol % | AA Conv % |
|---|---|---|---|---|---|
| E21 | 92.5 | 5 | 0.48 | 18.48 | 98.65 |
| E22 | 91.7 | 4.5 | 0.9 | 20.38 | 99.08 |
| E23 | 49.4 | 1.7 | 0.63 | 28.51 | 51.86 |
| E24 | 51.1 | 2.5 | 1.2 | 20.34 | 54.85 |
| E25 | 93.2 | 4.5 | 0 | 20.88 | 99.93 |

TABLE 14

Examples with Carbene and Additional Phosphine at High Temperatures Reaction Conditions

| Sample ID | Rh Source | Mass (g) | Moles ×10$^{-5}$ | Diphosphine | Mass (g) | Moles ×10$^{-5}$ |
|---|---|---|---|---|---|---|
| E21 | Rh(acac)(CO)$_2$ | 0.0110 | 4.3 | Gen4 | 0.0489 | 8.6 |
| E22 | (IMes)Rh(acac)(CO) | 0.0229 | 4.3 | Gen4 | 0.0485 | 8.6 |
| E23 | (IMes)Rh(acac)(CO) | 0.0233 | 4.3 | Gen3 | 0.0523 | 8.6 |
| E24 | (IMes)Rh(acac)(CO) | 0.0230 | 4.3 | DIOP | 0.0425 | 8.6 |
| E25 | (IMes)Rh(acac)(CO) | 0.0226 | 4.3 | Gen4 | 0.0488 | 8.6 |

| Sample ID | Ligand 2 | Mass (g) | Moles ×10$^{-5}$ |
|---|---|---|---|
| E21 | IMes | 0.0130* | 4.3 |
| E22 | | | |
| E23 | | | |
| E24 | | | |
| E25 | TPP | 0.0336 | 12.9 |

TABLE 15

Examples with 1-Octene

| Sample ID | Rh Source 4.3e-5 Moles | Ligand 1: Diphosphite 8.6e-5 Moles | Ligand 2: Carbene 4.3e-5 Moles | Ligand 3: Monophosphine 4.3e-5 Moles |
|---|---|---|---|---|
| C11 | Rh(CO)2acac | Gen4 | | |
| C12 | Rh(CO)2acac | Gen4 | | TPP |
| E26 | (IMes)Rh(acac)(CO) | Gen4 | | |
| E27 | (IMes)Rh(acac)(CO) | Gen4 | | TPP |

| Sample ID | Nonaldehyde mol % | 2-methyl-octanal mol % | C8 mol % | L:B Ratio mol % | 1-Octene Conv % |
|---|---|---|---|---|---|
| C11 | 75.9 | 22.7 | 0.3 | 3.34 | 98.77 |
| C12 | 80.1 | 18 | 0.3 | 4.45 | 98.47 |
| E26 | 85 | 11.1 | 0.3 | 7.65 | 96.08 |
| E27 | 79 | 12.7 | 0.3 | 6.2 | 91.72 |

TABLE 16

Examples with 1-Octene Reaction Conditions

| Sample ID | Rh Source | Mass(g) | Moles × 10$^{-5}$ | Diphosphine | Mass (g) | Moles × 10$^{-5}$ |
|---|---|---|---|---|---|---|
| C11 | Rh(acac)(CO)$_2$ | 0.0113 | 4.3 | Gen4 | 0.0485 | 8.6 |
| C12 | Rh(acac)(CO)$_2$ | 0.0114 | 4.3 | Gen4 | 0.0487 | 8.6 |
| E26 | (IMes)Rh(acac)(CO) | 0.0233 | 4.3 | DIOP | 0.0489 | 8.6 |
| E27 | (IMes)Rh(acac)(CO) | 0.0232 | 4.3 | Gen4 | 0.0485 | 8.6 |

| Sample ID | Ligand 2 | Mass (g) | Moles × 10$^{-5}$ |
|---|---|---|---|
| C11 | | | |
| C12 | TPP | 0.0340 | 12.9 |
| E26 | | | |
| E27 | TPP | 0.0337 | 12.9 |

TABLE 17

Abbreviations of Phosphines, Phosphites, and Diphosphines Used

| Abbreviations | Structures |
|---|---|
| Gen 4 | (structure) |
| Gen3 | (structure) |
| DPPB | (structure) |

TABLE 17-continued

Abbreviations of Phosphines, Phosphites, and Diphosphines Used

| Abbreviations | Structures |
|---|---|
| Cl-DIOP | |
| CF₃-DIOP | |
| Mod-DIOP | |
| DPEPhos | |
| DIOP | |
| TPP | |
| TXP | |
| T-pF-PP | |
| T-pCF₃-PP | |
| BIPHEPHOS | |

All of the compounds, complexes, and methods disclosed and claimed herein can be made and executed without undue experimentation in light of the present disclosure. While the compounds, complexes, and methods of this disclosure have been described in terms of preferred embodiments, it will be apparent to those of skill in the art that variations may be applied to the compounds, complexes, and methods, as well as in the steps or in the sequence of steps of the method described herein without departing from the concept, spirit, and scope of the disclosure. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 3,239,569
U.S. Pat. No. 3,239,570
U.S. Pat. No. 4,064,145
U.S. Pat. No. 4,215,077
U.S. Pat. No. 4,238,419
U.S. Pat. No. 4,306,087
U.S. Pat. No. 4,567,305
U.S. Pat. No. 4,678,857
U.S. Pat. No. 5,290,743
U.S. Pat. No. 5,504,261
U.S. Pat. No. 6,127,584
U.S. Pat. No. 6,225,509
U.S. Pat. No. 7,271,295
U.S. Pat. No. 7,279,606
U.S. Pat. No. 7,294,602
U.S. Pat. No. 7,790,932
Japanese Patent Application 57-117945
Japanese Patent Application 06-279344
Japanese Patent Application 06-279345
Allen, et al., *J. Organomet. Chem.,* 689:3203-3209, 2004.
Anderson, N. G., *Practical Process Research & Development—A Guide For Organic Chemists,* 2nd ed., Academic Press, New York, 2012.
Bitterman; et al., *J. Organomet. Chem.* 693: 2079-2090, 2008.
Bortenschlager, et. al., *J. Organomet. Chem.* 690:6233-6237, 2005a.
Bortenschlager, et. al., *J. Mol. Catal. A: Chem.* 233:67-71, 2005b.
Breit, et al., *Angew. Chem., Int. Ed.,* 44:1640-1643, 2005.
Brown and Wilkinson, *Tetrahedron Lett.,* 10:1725-1726, 1969.
Brown and Wilkinson, *J. Chem. Soc. A,* 2753-2764, 1970.
Cesar, et. al. RSC Catalysis Series (2011), 6, (N-Heterocyclic Carbenes), 228-251 NHC-cobalt, rhodium and iridium complexes in catalysis.
Chen, et al., *Organometallics,* 19:3459-3461, 2000.
Chen, et al., *Can. J. Chem.,* 83:943-957, 2005.
Coloquhuon, et al, *Carbonylations: Direct Synthesis of Carbonyl Compounds,* Plenum Press: New York, 1991.
Cotton and Wilkinson, *Advanced Inorganic Chemistry, Fifth Edition,* John Wiley & Sons, Inc, 1988.
Datt et al., *J. Organomet. Chem.* 690:3422-3426, 2005.
Dastgir, et al., *Organometallics,* 25:300-306, 2005.
Evans, et al., *J. Chem. Soc. A,* 3133-3142, 1968a.
Evans, et al., *J. Chem. Soc. A,* 2260-2265, 1968b.
Gil, et al., *Organometallics,* 27: 4131-4138, 2008.
Gil and Trzeciak, *Coord. Chem Rev.* 255:473-483, 2011.
Herrman, *Angew. Chem. Int. Ed.,* 41:1290-1309, 2002.
Hjortkjaer, *J. Mol. Catal.,* 5:377-384, 1979.
Leeuwen and Claver, *Rhodium Catalyzed Hydroformylation,* Kluwer Academic Publishers: Boston, 2000 Vol. 22.
*March's Advanced Organic Chemistry: Reactions, Mechanisms, and Structure,* 2007.
Neveling, et al., *Dalton Trans.,* 181-192, 2005.
Nolan, et. al., *Chem Rev.,* 109, 2009, 3612-3676
Poyatos, et al., *Organometallics,* 22:440-444, 2003.
Praetorius, et al., *Organometallics,* 26:1057-1061, 2007.
Praetorius, *Studies of the Coordination Chemistry and Catalytic Activity of Rhodium and Ruthenium N-Heterocyclic Carbene Complexes,* 2010.
Pruett, et al., In *Advances in Organometallic Chemistry,* Academic Press: Volume 17, 1-60, 1979.
Slaugh and Mullineaaux, *J. Orgnaomet. Chem.,* 13:469-477, 1968.
Weis, et al., *J. Am. Chem. Soc.,* 128:4188-4189, 2006.
Yagupsky, et al., *J. Chem. Soc. D—Chem. Comm.,* 1244-1245, 1969.
Zarka, et al., *Organometallics,* 23:4817-4820, 2004.

What is claimed is:

1. A method for the hydroformylation of a terminal alkene (C≤12) or a substituted terminal alkene (C≤12) to make an aldehyde, comprising:

reacting the terminal alkene (C≤12) or the substituted terminal alkene(C≤12) with carbon monoxide (CO) and hydrogen ($H_2$) in a reaction mixture comprising a rhodium complex and an N-heterocyclic carbene ligand to produce an aldehyde (C≤13) or a substituted aldehyde (C≤13) at a $H_2$/CO pressure from about 40 psi to about 600 psi;

wherein the reaction mixture further comprises a first auxiliary ligand, wherein the first auxiliary ligand is a phosphine (C≤30), a diphosphine (C≤50), a phosphite (C≤30), a diphosphite (C≤50), or a substituted version of any of these groups;

wherein the N-heterocyclic carbene ligand is selected from the group consisting of

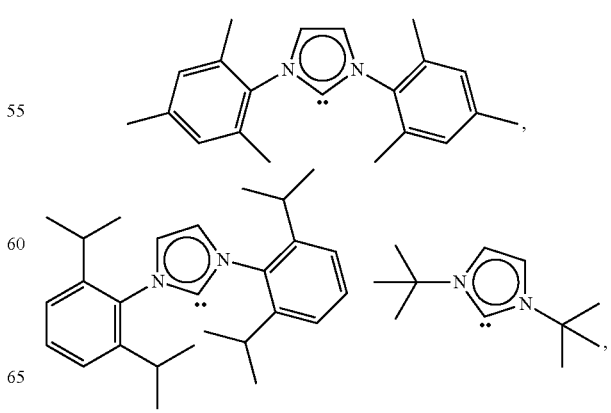

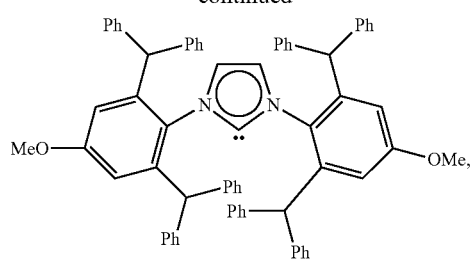

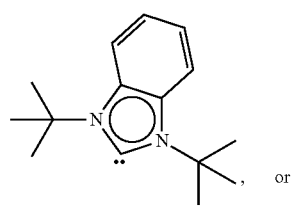

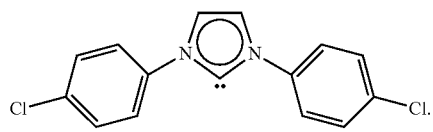

2. The method of claim 1, wherein the terminal alkene (C≤12) or substituted terminal alkene (C≤12) is allyl alcohol.

3. The method of claim 1, wherein the aldehyde (C13) or substituted aldehyde (C≤13) is 4-hydroxybutyraldehyde.

4. The method of claim 1, wherein the rhodium complex is a rhodium (I) complex with no halide ligands.

5. The method of claim 1, wherein the rhodium complex is Rh(CO)$_2$(acac), Rh(CO)$_2$COD, Rh(CO)$_2$(PPh3), or RhOAc.

6. The method of claim 1, wherein the first auxiliary ligand is:

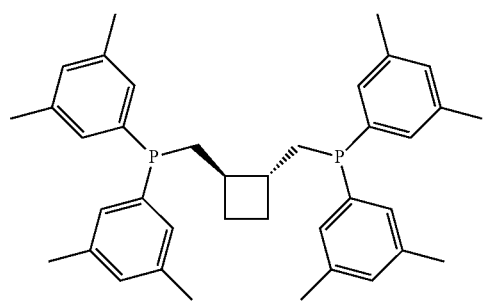

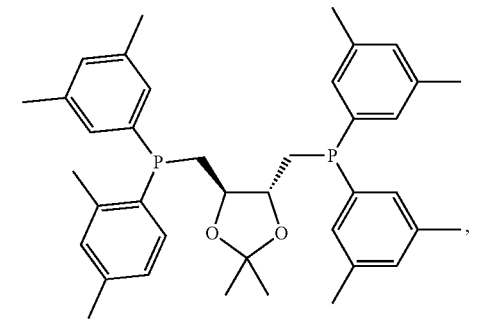

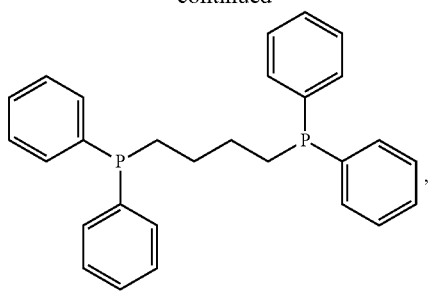

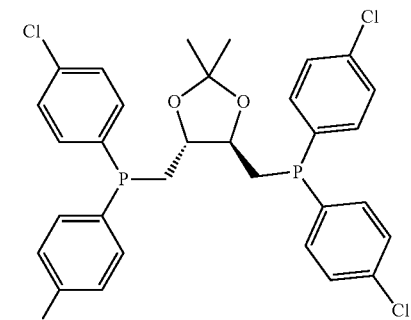

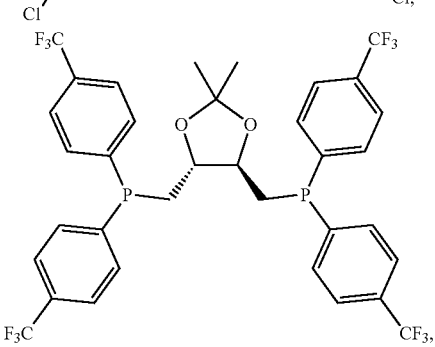

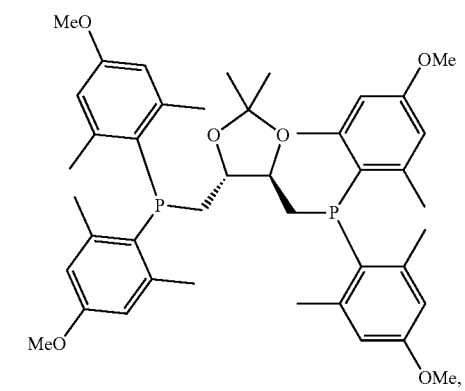

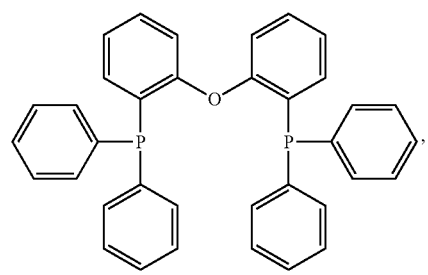

-continued
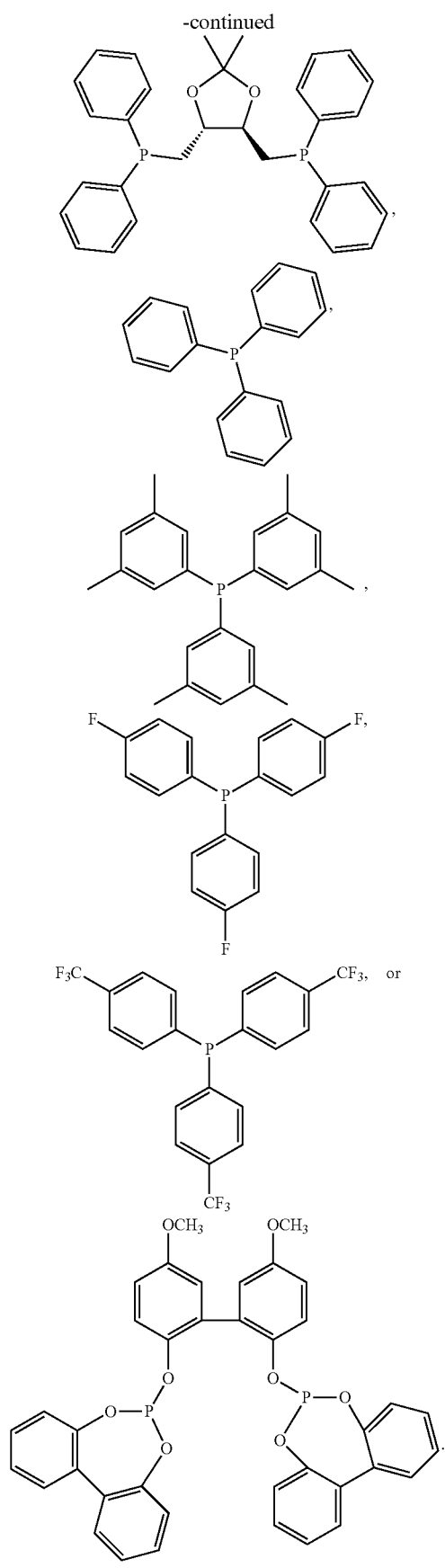
7. The method of claim 1, wherein the reaction mixture further comprises a second auxiliary ligand, wherein the second auxiliary ligand is a phosphine (C≤30), a diphosphine (C≤50), a phosphite (C≤30), a diphosphite (C<50), or a substituted version of any of these groups.
8. The method of claim 7, wherein the second auxiliary ligand is:
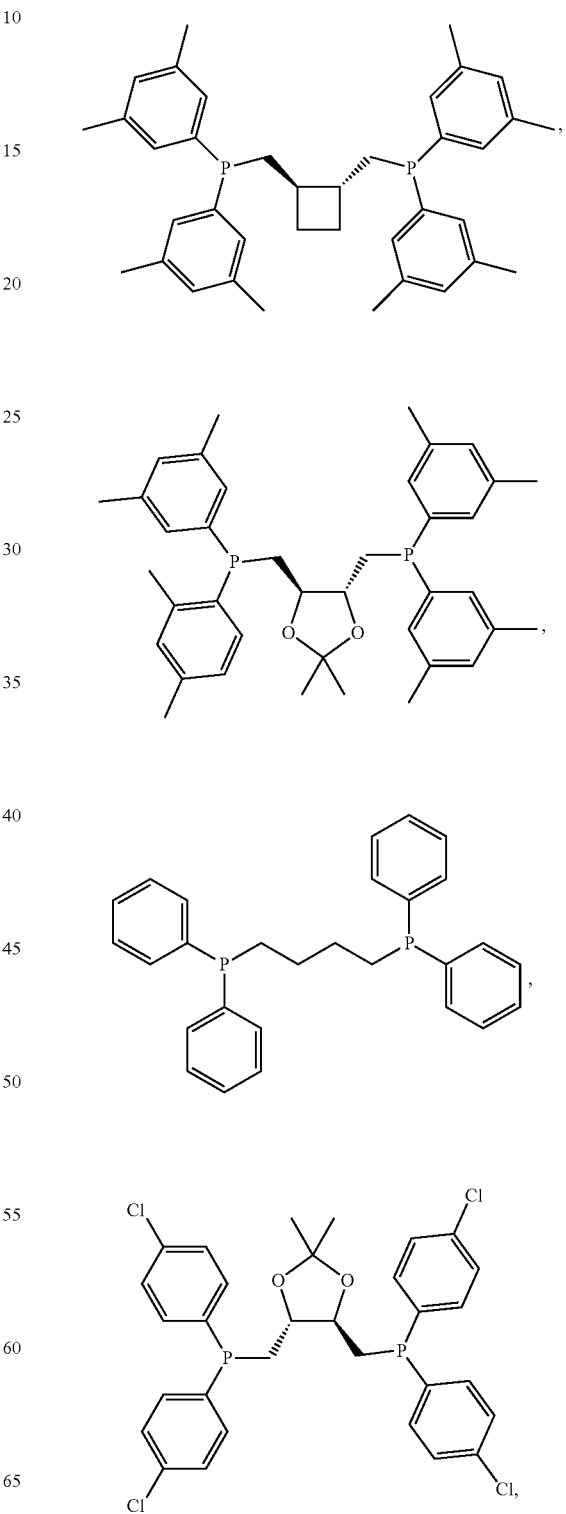

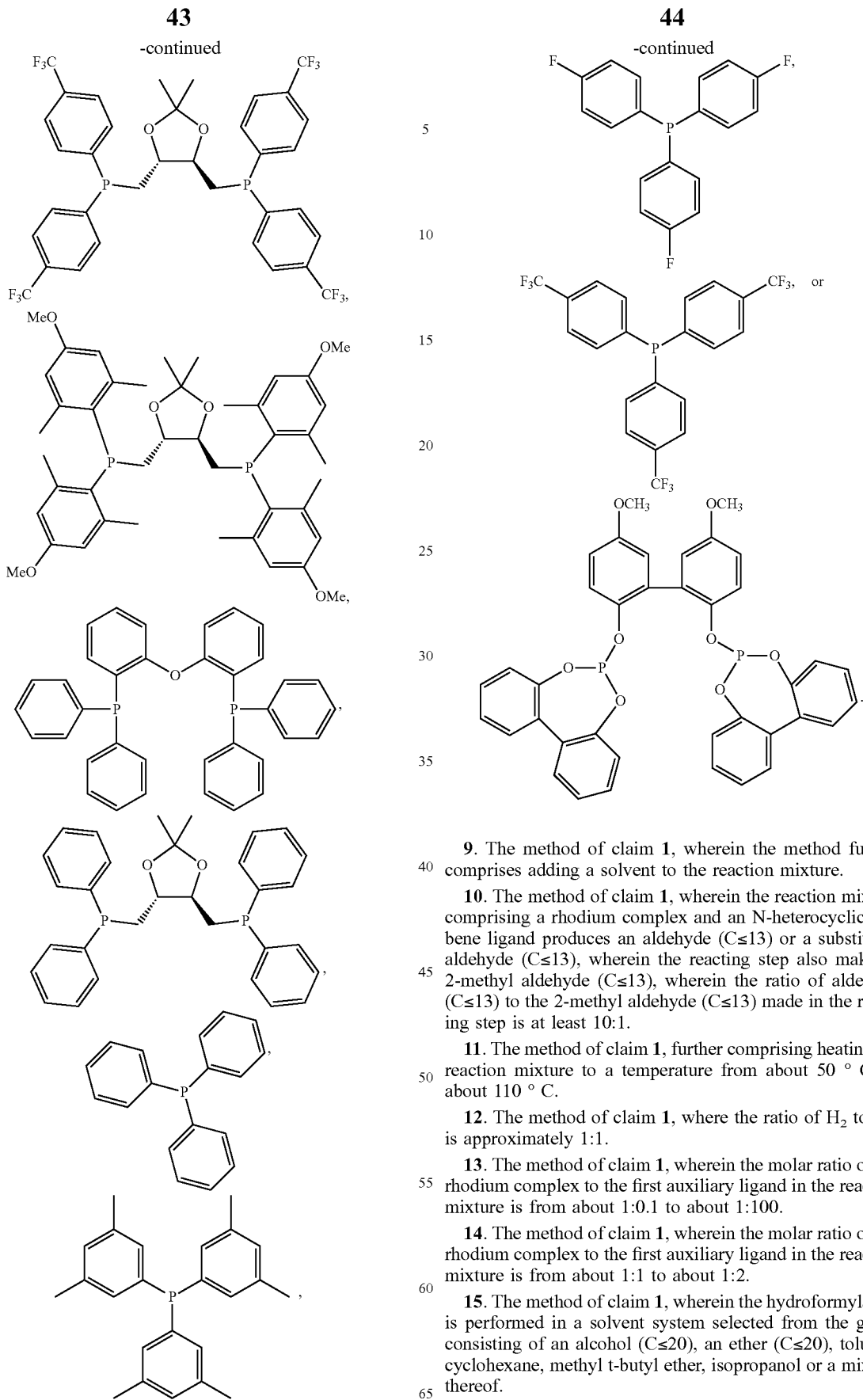

9. The method of claim 1, wherein the method further comprises adding a solvent to the reaction mixture.

10. The method of claim 1, wherein the reaction mixture comprising a rhodium complex and an N-heterocyclic carbene ligand produces an aldehyde (C≤13) or a substituted aldehyde (C≤13), wherein the reacting step also makes a 2-methyl aldehyde (C≤13), wherein the ratio of aldehyde (C≤13) to the 2-methyl aldehyde (C≤13) made in the reacting step is at least 10:1.

11. The method of claim 1, further comprising heating the reaction mixture to a temperature from about 50 ° C. to about 110 ° C.

12. The method of claim 1, where the ratio of $H_2$ to CO is approximately 1:1.

13. The method of claim 1, wherein the molar ratio of the rhodium complex to the first auxiliary ligand in the reaction mixture is from about 1:0.1 to about 1:100.

14. The method of claim 1, wherein the molar ratio of the rhodium complex to the first auxiliary ligand in the reaction mixture is from about 1:1 to about 1:2.

15. The method of claim 1, wherein the hydroformylation is performed in a solvent system selected from the group consisting of an alcohol (C≤20), an ether (C≤20), toluene, cyclohexane, methyl t-butyl ether, isopropanol or a mixture thereof.

* * * * *

UNITED STATES PATENT AND TRADEMARK OFFICE
CERTIFICATE OF CORRECTION

PATENT NO. : 9,765,005 B2  
APPLICATION NO. : 14/481528  
DATED : September 19, 2017  
INVENTOR(S) : Daniel F. White et al.

Page 1 of 1

It is certified that error appears in the above-identified patent and that said Letters Patent is hereby corrected as shown below:

In the Specification

| | | |
|---|---|---|
| Column 18 | Line 51 | Delete ""NHCH$_3$,"" and insert --NHCH$_3$,-- |
| Column 28 | Line 52 | In Table 3, delete "CI-DIOP" and insert --Cl-DIOP-- |
| Column 29 | Line 8 | In Table 8, delete "T-CF3-PP" and insert --T-CF$_3$-PP-- |
| Column 32 | Line 22 | In Table 10-continued, delete "CF3-DIOP" and insert --CF$_3$-DIOP-- |
| Column 32 | Line 5 | In Table 13, delete "Rh(CO)2acac" and insert --Rh(CO)$_2$acac-- |
| Column 33 | Line 33 | In Table 15, delete "Rh(CO)2acac" and insert --Rh(CO)$_2$acac-- |
| Column 33 | Line 34 | In Table 15, delete "Rh(CO)2acac" and insert --Rh(CO)$_2$acac-- |

In the Claims

| | | |
|---|---|---|
| Column 38 | Line 49 | In Claim 1, after "of", insert --:-- |
| Column 39 | Line 30 | In Claim 3, delete "(C13)" and insert --(C$\leq$13)-- |
| Column 39 | Line 36 | In Claim 5, delete "Rh(CO)$_2$(PPh3)," and insert --Rh(CO)$_2$(PPh$_3$),-- |
| Column 42 | Line 4 | In Claim 7, delete "(C<50)," and insert --(C$\leq$50),-- |

Signed and Sealed this  
Third Day of March, 2020

Andrei Iancu  
*Director of the United States Patent and Trademark Office*